US009249386B2

(12) United States Patent
Hattori et al.

(10) Patent No.: US 9,249,386 B2
(45) Date of Patent: Feb. 2, 2016

(54) SUBSTRATE FOR CELL TRANSFER

(75) Inventors: Hideshi Hattori, Tokyo (JP); Masatoshi Kuroda, Tokyo (JP)

(73) Assignee: DAI NIPPON PRINTING CO., LTD., Tokyo-to (JP)

( * ) Notice: Subject to any disclaimer, the term of this patent is extended or adjusted under 35 U.S.C. 154(b) by 1356 days.

(21) Appl. No.: 11/446,913

(22) Filed: Jun. 5, 2006

(65) Prior Publication Data

US 2007/0015277 A1      Jan. 18, 2007

(30) Foreign Application Priority Data

Jun. 6, 2005 (JP) ................................. 2005-165641

(51) Int. Cl.
*C12N 5/00* (2006.01)
(52) U.S. Cl.
CPC .......... *C12N 5/0068* (2013.01); *C12N 2533/30* (2013.01)
(58) Field of Classification Search
CPC ........................................................ C12N 11/08
See application file for complete search history.

(56) References Cited

U.S. PATENT DOCUMENTS

| 3,691,140 | A | * | 9/1972 | Silver ............................ 526/240 |
| 4,505,266 | A | * | 3/1985 | Yannas et al. .................. 128/898 |
| 4,789,601 | A | | 12/1988 | Banes |
| 5,096,941 | A | | 3/1992 | Harnden |
| 5,284,766 | A | | 2/1994 | Okano et al. |
| 5,470,739 | A | | 11/1995 | Akaike et al. |
| 5,512,131 | A | | 4/1996 | Kumar et al. |
| 5,580,770 | A | * | 12/1996 | DeFilippi ...................... 435/180 |
| 5,593,814 | A | | 1/1997 | Matsuda et al. |
| 5,602,029 | A | | 2/1997 | Miyamoto |
| 5,669,303 | A | | 9/1997 | Maracas et al. |
| 5,721,131 | A | | 2/1998 | Rudolph et al. |
| 5,725,788 | A | | 3/1998 | Maracas et al. |
| 5,900,160 | A | | 5/1999 | Whitesides et al. |
| 5,981,425 | A | | 11/1999 | Taoda et al. |
| 6,294,313 | B1 | | 9/2001 | Kobayashi et al. |
| 6,368,838 | B1 | | 4/2002 | Singhvi et al. |
| 6,541,033 | B1 | * | 4/2003 | Shah ............................ 424/486 |
| 6,863,437 | B2 | * | 3/2005 | Ohnishi et al. ................. 374/43 |
| 6,897,064 | B2 | * | 5/2005 | Yoshioka et al. ............. 435/397 |
| 6,951,712 | B2 | * | 10/2005 | Soane et al. ................... 435/1.3 |
| 7,022,523 | B2 | * | 4/2006 | Tsuzuki et al. ............... 435/401 |
| 2002/0182633 | A1 | | 12/2002 | Chen et al. |
| 2003/0089259 | A1 | | 5/2003 | Damme et al. |
| 2004/0235167 | A1 | | 11/2004 | Miyake et al. |
| 2005/0186674 | A1 | | 8/2005 | Miyake et al. |
| 2005/0208656 | A1 | | 9/2005 | Miyake et al. |
| 2005/0255594 | A1 | | 11/2005 | Miyake et al. |
| 2005/0266319 | A1 | | 12/2005 | Miyake et al. |
| 2005/0279730 | A1 | | 12/2005 | Miyake et al. |
| 2006/0019390 | A1 | | 1/2006 | Miyake et al. |
| 2006/0183219 | A1 | | 8/2006 | Miyake et al. |
| 2007/0122901 | A1 | | 5/2007 | Morita et al. |
| 2008/0118474 | A1 | * | 5/2008 | Okano et al. .................. 424/93.7 |

FOREIGN PATENT DOCUMENTS

| EP | 1 246 011 | A2 | | 10/2002 |
| EP | 1 302 535 | A1 | * | 4/2003 |
| JP | 10-12545 | | | 1/1989 |
| JP | 2-211865 | | | 8/1990 |
| JP | 2-245181 | | | 9/1990 |
| JP | 3-7576 | | | 1/1991 |
| JP | 03-198771 | | | 8/1991 |
| JP | 04-4869 | | | 1/1992 |
| JP | 04-94679 | | | 3/1992 |
| JP | 04-126071 | | | 4/1992 |
| JP | 04-126074 | | | 4/1992 |
| JP | 05-038278 | A | | 2/1993 |
| JP | 5-176753 | | | 7/1993 |
| JP | 6-335381 | | | 12/1994 |
| JP | 7-75547 | | | 3/1995 |
| JP | 07-099962 | | | 4/1995 |
| JP | 7-308186 | | | 11/1995 |
| JP | 08-009960 | | | 1/1996 |
| JP | 9-240125 | | | 9/1997 |
| JP | 2002-184752 | | | 6/2002 |
| JP | 2002-253204 | | | 9/2002 |
| JP | 2002-274077 | | | 9/2002 |
| JP | 2002-355026 | | | 12/2002 |

(Continued)

OTHER PUBLICATIONS

Woon-Seok Yeo, et al; " Electroactive Monolayer Substrates that Selectively Release Adherent Cells", Chembiochem 2001, No. 7/8, pp. 590-593.

Kyung-Soon Cho, et al; "The Effect of Energy Irradiation on the Volum Resistivity Properties of Low Density Polyethylene Film", Conference Record of the 1998 IEEE International Symposium on Electrical Insulation, Arlington, Virginia, USA, Jun. 7-10, 1998, pp. 194-196.

Dan V. Nicolau, et al; "Control of the neuronal cell attachment by functionality manipulation of diazo-naphtho-quinone/novolak photoresist surface", Biosensors & Bioelectronics vol. 11. No. 12, pp. 1237-1252, 1996.

(Continued)

*Primary Examiner* — Ralph Gitomer

(74) *Attorney, Agent, or Firm* — Ladas & Parry LLP

(57) ABSTRACT

A main object of the present invention is to provide a cell transfer substrate capable of transplanting cells, maintaining a pattern as it is, on a living body tissue or the like, even when: the size of the cell sheet is extremely small; the cells are cultured sparsely; the cells are in a form of a small colony; or the cells are cultured in a pattern, for example, as a blood vessel, a vessel network such as a lymphatic vessel, or a nerve network, and to provide a substrate for cell transfer to be used for the cell transfer substrate. In order to achieve the above-mentioned object, the present invention provides a substrate for cell transfer comprising: a polymer base material; an intermediate layer formed on the polymer base material; and a cell transfer layer formed on the intermediate layer.

14 Claims, 2 Drawing Sheets

(56) References Cited

FOREIGN PATENT DOCUMENTS

| | | |
|---|---|---|
| JP | 2002-355031 | 12/2002 |
| JP | 2002-542883 | 12/2002 |
| JP | 2003-9860 | 1/2003 |
| JP | 2003-039399 | 2/2003 |
| JP | 2003-228172 | 8/2003 |
| JP | 2003-295428 | 10/2003 |
| JP | 2003-339373 | 12/2003 |
| JP | 2003038170 | 12/2003 |
| JP | 2004-51 | 1/2004 |
| JP | 2004-033136 A | 2/2004 |
| JP | 2004-57019 | 2/2004 |
| JP | 2004-344025 | 12/2004 |
| WO | 98/51785 | 11/1998 |
| WO | 2005/038011 A1 | 4/2005 |

OTHER PUBLICATIONS

B.J. Spargo, etl al; "Spatially controlled adhesion, spreading, and differentiation of endothelial cells on self-assembled molecular monolayers" Proc. Natl. Acad. Sci. USA, vol. 91, pp. 11070-11074, Nov. 1994, Cell Biology.

G. Sagvolden, et al; "Cell adhesion force microscopy", Proc. Natl. Acad. Sci. USA, vol. 96, pp. 471-476, Jan. 1999 Biophysics.

W. Chris Wilson, Jr. et al; "Cell and Organ Printing 1: Protein and Cell Printers", The Anatomical Record, Part A 272A: 491-496(2003).

\* cited by examiner

SUBSTRATE FOR CELL TRANSFER

BACKGROUND OF THE INVENTION

1. Field of the Invention

The present invention relates to a cell transfer substrate used for processing or transplantation of a cell, capable of transferring the cell while retaining its activity, and to a substrate for cell transfer, capable of forming the cell transfer substrate.

2. Description of the Related Art

Recently, the technique of transplanting a cultured cells formed into a tissue, as they are, attracts the attention. When an artificial skin or an artificial blood vessel using synthetic polymer or the like is transplanted, rejection may occur after the transplantation so as to induce problem of application difficulties. However, when a cultured cell tissue prepared by culturing the cells of the patient to form a tissue, there is no risk of the rejection so that it can be used preferably for the transplantation.

However, the above-mentioned cultured cell tissue or the like that are cultured on a cell culture substrate involves a problem that it is difficult to transplant to a living body tissue or to transfer onto another culture substrate for processing. The problem arises because, for example, at recovery of the cultured cell tissue cultured in a pattern on a cell culture substrate, it is difficult to peel off only the cultured cell tissue from the cell culture substrate.

Therefore, a method for recovering a cultured cell tissue by peeling off the same from the cell culture substrate using, for example, a proteolytic enzyme, a chemical or the like has been proposed. However, according to this method, there is a risk that the cell may be modified or damaged by the above-mentioned chemical, enzyme or the like so as to deteriorate the function inherent to the cell. Moreover, there is also a problem that the treatment processes will be complicated, that there is a risk of contamination or the like.

Moreover, Japanese Patent Application Laid-Open (JP-A) No. 2003-38170 proposes a method in which a cell culture supporting member, wherein a pattern of a thermosensitive polymer is formed on a base material, is prepared, the cells are cultured on the cell culture supporting member, and the cell tissue is peeled off. According to the method, by changing the temperature of the thermosensitive polymer while the cells cultured on a thermosensitive polymer are adhered on, for example, a polymer film or the like, the sheet-like cell (cell sheet) can be removed from the thermosensitive polymer so that the above-mentioned cell sheet can be adhered on the polymer film by the function of the surface tension of the culture medium. Thereafter, by adhering the cell sheet, which is supported on the polymer film side, to the culture substrate, the living body tissue or the like, the above-mentioned cell sheet can be transferred onto another culture substrate or transplanted on the living body tissue. However, according to the method, there are problems that, when the size of the cell sheet is extremely small, or the cells are cultured sparsely or in a form of a small colony, due to the insufficient function of the surface tension with respect to the polymer film, the cells slip on the polymer film, so as not to be adhered on the polymer film side. Moreover, there is also a problem that, when the cells cultured in a pattern, for example, as a blood vessel, a vessel network such as a lymphatic vessel, or a nerve network, are adhered to the polymer film, the pattern-like cells slip on the polymer film or the like so that the pattern cannot be maintained.

SUMMARY OF THE INVENTION

Therefore, provision of a cell transfer substrate capable of transplanting cells, maintaining a pattern as it is, on a living body tissue or the like, even when: the size of the cell sheet is extremely small; the cells are cultured sparsely; the cells are in a form of a small colony; or the cells are cultured in a pattern, for example, as a blood vessel, a vessel network such as a lymphatic vessel, or a nerve network, and provision of a substrate for cell transfer to be used for the cell transfer substrate are desired.

In order to achieve the above-mentioned object, the present invention provides a substrate for cell transfer comprising: a polymer base material; an intermediate layer formed on the polymer base material; and a cell transfer layer formed on the intermediate layer.

In general, a polymer base material has a poor wettability with respect to a water based coating material or a high polarity coating material so that the wettability with respect to the cell transfer layer forming material, used for forming a cell transfer layer, used in the present invention is poor as well. Therefore, it is difficult to evenly form the cell transfer layer, having the cell transfer properties, on the above-mentioned polymer base material. However, in the present invention, since the intermediate layer is formed in between the above-mentioned polymer base material and cell transfer layer, the wettability of the surface on which the cell transfer layer will be formed can be adjusted, so that the cell transfer layer can be formed evenly. Moreover, since the above-mentioned cell transfer layer is formed evenly, the cells can be cultured stably on the cell transfer layer or the cells can be cultured in a purposed pattern so that the cultured cells can be transferred onto another cell culture substrate or directly transplanted onto a living body tissue in an active state.

In the above-mentioned invention, the above-mentioned cell transfer layer may be a layer containing a thermosensitive polymer. In this case, the adhesive properties of the above-mentioned cell transfer layer with respect to the cells can be varied according to the temperature so that the cell tissue cultured on the cell transfer layer can be transferred efficiently.

Moreover, in the above-mentioned invention, the above-mentioned cell transfer layer may be a layer containing a polyalkylene glycol or a derivative thereof. In this case, since the above-mentioned cell transfer layer has extremely weak cell adhesive properties, the cell tissue cultured on the cell transfer layer can be efficiently transferred onto a transfer receptor.

The present invention provides a cell transfer substrate, wherein a cell is adhered to the cell transfer layer of any one of the above-described substrate for cell transfer.

In the present invention, since the above-mentioned cell transfer layer is formed evenly, the cells can be cultured stably and adhered evenly on the cell transfer layer. Therefore, a cell transfer substrate capable of directly transplanting the cells cultured on the cell transfer layer, onto a transfer receptor in an active state, can be provided.

According to the present invention, since the above-mentioned intermediate layer is formed, the above-mentioned cell transfer layer can be formed evenly. Therefore, by using the substrate for cell transfer of the present invention, the cells can be cultured stably or can be formed in a purposed pattern. Thus, the effect, that the cultured cells can be transferred onto another cell culture substrate, or directly transferred onto a living body tissue in an active state, can be achieved.

DESCRIPTION OF THE PREFERRED EMBODIMENT

The present invention relates to a cell transfer substrate used for processing or transplantation of a cell, capable of transferring the cell while retaining its activity, and to a substrate for cell transfer, capable of forming the cell transfer substrate. Hereinafter, each will be explained respectively.

A. Substrate for Cell Transfer

First, the substrate for cell transfer of the present invention will be explained. The substrate for cell transfer of the present invention comprises: a polymer base material; an intermediate layer formed on the above-mentioned polymer base material; and a cell transfer layer formed on the above-mentioned intermediate layer.

Figure 1:
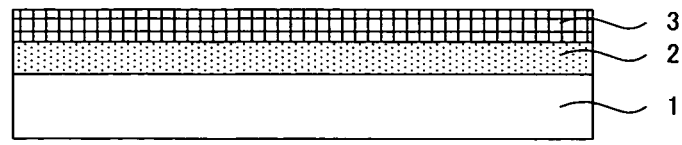
FIG. 1 is a schematic cross-sectional view showing an example of a substrate for cell transfer of the present invention.
Figure 2A:
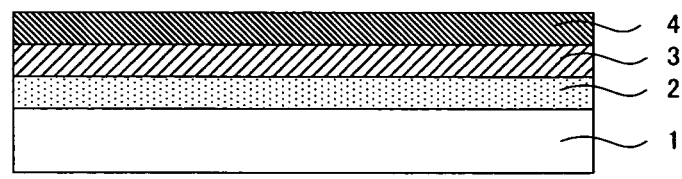
FIG. 2 is an explanatory diagram for explaining a substrate for cell transfer of the present invention.
Figure 2B:
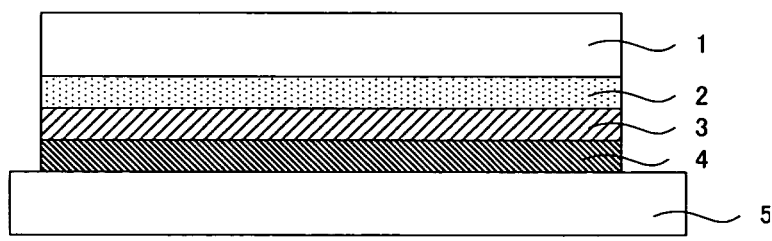
Figure 2C:
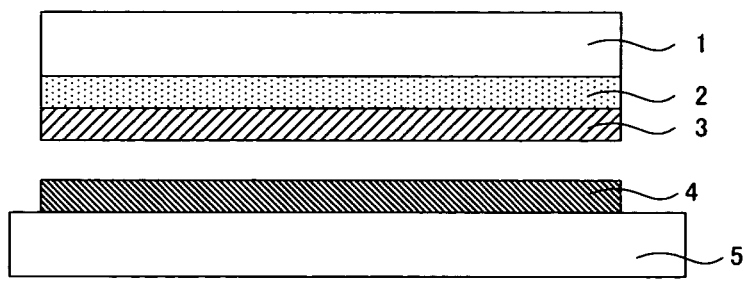

For example, as shown in FIG. 1, the substrate for cell transfer of the present invention comprises: a polymer base material 1; an intermediate layer 2 formed on the polymer base material 1; and a cell transfer layer 3 formed on the intermediate layer 2. For example as shown in FIG. 2, the substrate for cell transfer of the present invention is used for: preparing a cell transfer substrate by adhering cells 4 on the above-mentioned cell transfer layer 3 (FIG. 2A); adhering the cells 4, which are cultured on the cell transfer substrate, onto a transfer receptor 5 such as a living body tissue and a cell culture substrate (FIG. 2B); and transferring only the cells 4 onto the transfer receptor 5 side (FIG. 2C).

In the present invention, since the cell transfer layer having the cell transfer properties is formed, the cell cultured on the cell transfer layer can be transferred directly to the transfer receptor such as the cell culture substrate and the living body tissue. Thus, the cells can be transplanted onto the living body tissue or the like, maintaining the pattern as it is, even when: the size of the cell pattern cultured on the cell transfer layer is extremely small; the cells are cultured sparsely; the cells are in a form of a small colony; or the cells are cultured in a pattern, for example, as a blood vessel, a vessel network such as a lymphatic vessel, or a nerve network.

Here, in general, a polymer base material has a poor wettability with respect to a water based coating material or a high polarity coating material so that the wettability with respect to the cell transfer layer forming material used for forming a cell transfer layer used in the present invention is poor as well. Thus, it is difficult to evenly form the cell transfer layer. However, in the present invention, since the above-mentioned intermediate layer is provided, the wettability of the surface, on which the above-mentioned cell transfer layer is formed, can be adjusted so that the cell transfer layer can be formed evenly. Therefore, by using the substrate for cell transfer of the present invention, the cells can be cultured stably on the cell transfer layer or the cells can be cultured in a purposed pattern so that the cells can be transferred onto a transfer receptor in an active state.

Moreover, in the present invention, since a polymer base material is used for the above-mentioned substrate for cell transfer, the flexibility of the substrate for cell transfer can be improved so that a cell tissue can be transferred onto a living body tissue having a curved surface or the like. Thus, there is an advantage that it can be used for various applications.

Hereinafter, the substrate for cell transfer of the present invention will be explained in detail for each configuration.

1. Intermediate Layer

First, the intermediate layer used for the substrate for cell transfer of the present invention will be explained. The intermediate layer used in the present invention is not particularly limited as long as it can be formed on the polymer base material and the cell transfer layer to be described layer can be formed evenly thereon.

It is preferable that the intermediate layer used in the present invention has the contact angle with a liquid in a predetermined range. Specifically, it is preferable that the contact angle with a liquid (water) having a 72.75 mN/m (literature value) surface tension is in a range of 1° to 50°, and in particular, in a range of 5° to 45°. Thereby, the wettability of the intermediate layer and the cell transfer layer forming material for forming a cell transfer layer can be provided preferably so that the cell transfer layer can be formed evenly on the intermediate layer. The above-mentioned contact angle with water is obtained from the measurement value, within 1 minute from dropping water droplets from a micro syringe, using a commercially available contact angle measuring device such as CA-Z type manufactured by Kyowa Interface Science, Co., Ltd.

Such an intermediate layer can be, for example, a layer containing a polarity polymer, a layer containing an inorganic oxide, or a layer of a composite substance thereof or the like. As the above-mentioned polarity polymer, for example, a polyvinyl alcohol, a polymethacrylic acid-2-hydroxy ethyl, a polyvinyl pyrrolidone, a polyacrylic acid, a polystyrene sulfonic acid, a polyridine, a polyethylene imine, a polyallyl amine or the like can be presented. Moreover, as the above-mentioned inorganic oxide, for example, a silicone based oxide, a titanium based oxide, an aluminum based oxide, a phosphoric acid oxide or the like can be presented. In particular, as the material for the intermediate layer of a silicone based oxide, an organic silicon compound such as a hexamethyl disiloxane, a tetramethyl disiloxane or the like is preferable. Moreover, the above-mentioned inorganic oxide may be used together with a material having a methyl group, a fluoroalkyl group or the like.

The method for forming such an intermediate layer is not particularly limited as long as it is a method capable of evenly forming the above-mentioned intermediate layer, and thus, it can be selected optionally according to the kind of the above-mentioned intermediate layer. Specifically, a wet coating method such as a roll coating method, a die coating method and a bead coating method, or a dry coating method such as an adsorption method, a layer-by-layer self-assembling method, a sputtering method, a physical deposition method (PVD method), a chemical deposition method (CVD method), a method using a plasma and the like can be presented.

The surface of the above-mentioned intermediate layer may be flat. However, in order to adjust the surface wettability of the intermediate layer, minute convexoconcave may be provided on the surface. The surface roughness of the intermediate layer in this case is preferably in a range of 5 nm to 300 nm, in particular, in a range of 15 nm to 250 nm. Thereby, the contact angle of the intermediate layer surface and a liquid can be provided in the above-mentioned range. As the method for forming the above-mentioned convexoconcave on the surface of the above-mentioned intermediate layer, for example, a method in which the intermediate layer containing the above-mentioned polarity polymer is dry etched with an oxygen plasma or the like, a method in which the intermediate layer is formed by the adsorption method or the like can be presented. The above-mentioned surface roughness here can be obtained based on the value measured by the tapping mode using commercially available atomic force microscope such as SPI3800N manufactured by Seiko Instruments Inc., or the measurement value of the height difference in the cross section with a commercially available scanning electron microscope.

Moreover, the above-mentioned intermediate layer may be formed on the entire surface of the polymer base material to be described later, or it may be formed in a pattern. In the case the intermediate layer is formed in a pattern, the cell transfer layer to be described later can be formed only on the region provided with the intermediate layer. Thus, there is an advantage that the cells can be cultured and transferred in a pattern. The method for patterning the above-mentioned intermediate layer can be same as a common patterning method.

Moreover, the film thickness of the above-mentioned intermediate layer is preferably about 1 nm to 500 nm, more preferably about 2 nm to 300 nm, and particularly preferably about 5 nm to 200 nm. When the layer is thinner than the above-mentioned film thickness, it is difficult to form the intermediate layer evenly so that the cell transfer layer to be described later can hardly be formed evenly. Moreover, when the layer is thicker than the above-mentioned range, cracking or the like can easily be generated so that the flexibility of the substrate for cell transfer may be deteriorated.

2. Cell Transfer Layer

Next, the cell transfer layer used in the present invention will be explained. The cell transfer layer is not particularly limited as long as: it is formed on the above-mentioned intermediate layer; the cells can be adhered and cultured on the surface thereof; and the cultured cells can be transferred to another cell culture substrate, a living body tissue or the like without deteriorating the function thereof. In the present invention, the cell transfer properties denotes the nature capable of contacting the cells adhered and cultured on a substrate, with a transfer receptor, still alive and being adhered to the substrate, and then, transferring the cells to the transfer receptor after a predetermined time. In the present invention, when 80% or more of the cells adhered to the substrate are transferred to the transfer receptor within 48 hours at latest from the contacting of the cells adhered and cultured on the substrate with the transfer receptor, the substrate is stated as having the cell transfer properties. The above-mentioned cell transfer properties can be evaluated by peeling off the substrate after contacting the cells adhered to the substrate with the transfer receptor for a predetermined time, and observing the number of the cells present on the surface of the substrate and the transfer receptor in a predetermined range, where the substrate and the transfer receptor were in contact via the cells, with a commercially available microscope. In the case the transfer receptor is a living body tissue, the microscope observation of the transfer receptor may be difficult. In this case, the evaluation can be carried out by preliminarily counting the number of the cells in a predetermined range of the substrate before the transfer operation, and counting the number of the cells remaining on the above-mentioned range of the substrate.

As to the cell transfer layer used in the present invention, it is preferable that the time necessary for transferring 80% or more of the cells cultured on the cell transfer layer is 24 hours or less, and more preferably 6 hours or less.

Here, the material used for the above-mentioned cell transfer layer is not particularly limited as long as it has the above-mentioned cell transfer properties. As such a material, for example, a material containing fluorine and oxygen or the like can be presented. Specifically, an ionic fluorine polymer such as NAFION (product name), or a fluorine based silane coupling agent, a gel containing a fluoroalkyl chain and a hydroxyl group, an ethylene glycol based silane coupling agent or the like can be presented.

Moreover, in the present invention, as the above-mentioned cell transfer layer, a hydrophilic polymer material can be used as well. Specifically, a thermosensitive polymer such as a poly(N-isopropyl acrylic amide), or a polyalkylene glycol and a derivative thereof such as a polyethylene glycol, a polyethylene glycol-polypropylene glycol block copolymer, an amphoteric ion polymer such as MPC POLYMER (product name) having a phosphoric fatty polarity group or the like can be presented.

Moreover, the above-mentioned cell transfer layer may contain a photocatalyst. Specifically, the above-mentioned cell transfer layer may be a layer comprising a mixture of the above-mentioned material having the cell transfer properties and photocatalyst fine particles, the above-mentioned cell transfer layer may be a layer comprising two layers, that are, a photocatalyst-containing layer containing at least a photocatalyst and a layer comprising the above-mentioned material having the cell transfer layer. As the photocatalyst to be used at the time, for example, those mentioned in JP-A No. 2001-249219 can be used as well.

In the present invention, among the above-mentioned examples, in particular, a layer containing a thermosensitive polymer is preferable. Thereby, after culturing the cells on the cell transfer layer, the adhesive properties between the cells and the cell transfer layer can be varied by changing the temperature so that the cells can be transferred directly to the transfer receptor efficiently.

Moreover, in the present invention, a polyalkylene glycol and a derivative thereof may be used. In particular, it is preferable to use a polyethylene glycol. Although these materials have high cell adhesion-inhibiting properties, by the modification using the above-mentioned photocatalyst or the like, it is possible to form a cell transfer layer having extremely weak cell adhesive properties. As a result, the cells can be transferred directly to the transfer receptor efficiently.

The method for forming the above-mentioned cell transfer layer can be selected optionally according to the kind of the above-mentioned cell transfer layer, the shape of the substance for cell transfer or the like. In general, a wet coating method such as a roll coating method, a die coating method and a bead coating method, or an adsorption method, an layer-by layer self-assembling method or the like can be used.

Figure 3:
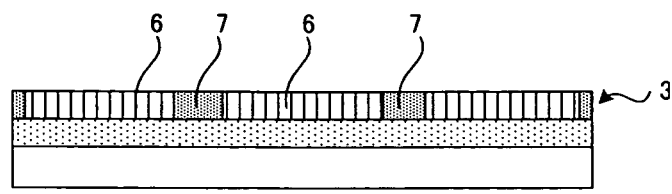
FIG. 3 is a schematic cross-sectional view showing another example of a substrate for cell transfer of the present invention.

Moreover, the entire surface of the above-mentioned cell transfer layer may be a cell adhesion region having the adhesive properties to a cell. However, for example as shown in FIG. 3, the cell transfer layer 3 may comprise a cell adhesion region 6 having the adhesive properties to a cell, and a cell adhesion-inhibiting region 7 having no adhesive properties to a cell. In the case the cell transfer layer comprises the above-mentioned cell adhesion region and cell adhesion-inhibiting region, the cells can be adhered and cultured on only the cell adhesion region so that the cells can be transferred in a pattern.

Here, the cell adhesion region used for culturing and transferring the above-mentioned cells can be selected optionally according to the kind of the cells to be transferred. Generally, it is a region wherein the contact angle of the cell transfer layer surface with water is about 10° to 60°, and more preferably in a range of 15° to 55°. Since the contact angle with water is provided, the cell can be adhered and cultured on the cell transfer layer so as to be transferred to the transfer receptor in an active state. Moreover, in the case the contact angle with water is larger than the above-mentioned range, although the cells can be adhered onto the cell transfer layer, they can hardly be transferred. In the case the contact angle with water is smaller than the above-mentioned range, the cells can hardly be adhered onto the cell transfer layer. Particularly when the pattern of the transferring cells is composed of lines or dots with the width of 1 mm or less, the contact angle of the above-mentioned cell adhesion region surface with water is preferably in a range of 10° to 45°, more preferably in a range of 15° to 35°. According to the range, the cells can be transferred in a highly precise pattern.

Moreover, when the cell transfer layer has the above-mentioned cell adhesion-inhibiting region, it is preferable that the cell adhesion-inhibiting region is a region wherein the contact angle thereof with a liquid is larger than the contact angle with a liquid of the above-mentioned cell adhesion region by about 50° to 160°, more preferably by about 60° to 150°. Otherwise, it is preferable that the cell adhesion-inhibiting region is a region wherein the contact angle thereof with a liquid is smaller than the contact angle with a liquid of the above-mentioned cell adhesion region by about 10° to 40°, more preferably by about 15° to 35°. This is because such region will have poor adhesive properties to a cell.

Examples of the method for forming the above-mentioned cell adhesion region and cell adhesion-inhibiting region are as follows: a method in which a layer having the adhesion-inhibiting properties with the cells is formed, and then, the contact angle with a liquid of only the portion to be the cell adhesion region is varied; and a method in which a layer having the cell adhesive properties is formed, and then, the contact angle with a liquid of only the portion to be the cell adhesion-inhibiting region is varied. For example, the following examples can be listed: a method in which the cell transfer layer is formed by using the above-mentioned materials, and then, the contact with a liquid of only the portion, to be the cell adhesion region or to be the cell adhesion-inhibiting region, is lowered; a method in which the cell transfer layer is formed by using the above-mentioned materials, and then, the contact with a liquid of only the portion, to be the cell adhesion region or to be the cell adhesion-inhibiting region, is raised.

As a method for raising the contact angle with a liquid of the cell transfer layer as mentioned above, for example, a method in which minute convexoconcave is formed on the cell transfer layer surface, or the like can be presented. For example, the method disclosed in the literature of: Japanese Journal of Applied Physics, part 2, vol. 32, L614-L615, 1993, Ogawa, et. al.; and Langmuer, vol. 19, 10624-10627, 2003, Teshima, et. al., can be used.

Moreover, as the method for lowering the contact angle with a liquid of the above-mentioned cell transfer layer, following examples can be listed: a method in which a group having the liquid repellency is decomposed or modified, utilizing the action of a photocatalyst upon irradiation with energy; a method in which a group having the liquid repellency is decomposed or modified by the heat irradiation, the ultraviolet ray irradiation, the electron beam irradiation. As mentioned above, in the case a photocatalyst is contained in the cell transfer layer, the contact angle with a liquid of the cell transfer layer can be lowered, utilizing the action of the photocatalyst in the cell transfer layer. Moreover, in the case a photocatalyst is not contained in the cell transfer layer, the contact angle with a liquid of the cell transfer layer can be lowered using, for example: the patterning method disclosed in JP-A No. 2001-249219 which uses a photocatalyst; and the patterning method disclosed in JP-A No. 2003-222626 which used a photocatalyst, or the like. Moreover, since the patterning operation by the heat irradiation, the ultraviolet ray irradiation, the electron beam irradiation or the like, can be same as a common patterning method using these energies, detailed explanation is omitted here.

Moreover, the above-mentioned cell transfer layer may be formed on the entire surface of the above-mentioned intermediate layer, or it may be formed in a pattern. The patterning method may be same as a common patterning method.

Here, the film thickness of the above-mentioned cell transfer layer may be selected optionally according to the kind, etc. of the cell transfer layer. Generally, it is about 1 nm to 1,000 nm, preferably about 1.5 nm to 750 nm, and particularly preferably about 20 nm to 500 nm. According to the above-mentioned range, the cells can be cultured and transferred stably.

3. Polymer Base Material

Next, the polymer base material used in the present invention will be explained. As to the polymer base material used in the present invention, the kind of the polymer base material or the like is not particularly limited as long as the above-mentioned intermediate layer can be formed evenly and it can be sterilized by a known method. As the known sterilizing method, for example, a sterilizing method by irradiating a γ ray, a sterilizing method by irradiating an ultraviolet ray, a sterilizing method by irradiating an electron beam, a sterilizing method by an autoclave or the like can be presented.

The polymer base material can be selected optionally based on the function needed for the substrate for cell transfer, such as the flexibility and the transparency. For example, a polypropylene, a polymethyl pentene, a polypropylene copolymer, a fluorine resin such as a Teflon (registered trademark) and an ethylene-tetrafluoroethylene copolymer, a polycarbonate, an acetal resin, a polysulfone, a polyvinyl chloride, a silicone resin, a polystyrene, a styrene-acrylonitrile copolymer, an acrylic resin such as a methyl polymethacrylate, a polyurethane, a polyester, a polyimide, a polyglycol acid, a polylactic acid, a collagen, a living body absorbing type polymer such as an elastin or the like can be used. Moreover, a non-woven fabric, a woven fabric, or the like can be used as well.

Moreover, the above-mentioned polymer base material may be porous, and the polymer base material is particularly useful in the case of co-culturing using the feeder cells is needed before transferring the cultured cells onto the cell transfer layer. Moreover, in this case, at the time of the cell transfer operation, there is also an effect that the culturing medium and the oxygen can be evenly spread to every cell. In this case, the average pore size depends on the kind of the cell. However, it is generally preferably 0.1 μm to 5 μm, and more preferably 0.2 μm to 1.5 μm. In the case the pore size is less than 0.1 μm, the supplying efficiency of the nutrition and the liquid factor to the cultured cells becomes inferior. Moreover, in the case the pore size is more than 5 μm, the ratio of the cultured cells adhered to the inside of the pores or the rear side of the polymer base material is increased so that the cultured cells cannot be transferred efficiently.

Figure 4:
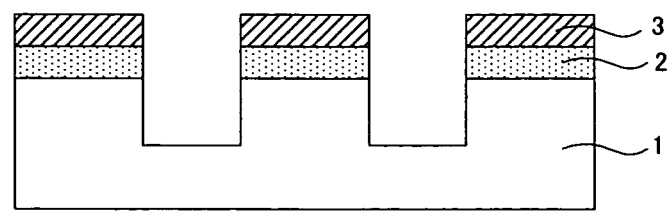
FIG. 4 is a schematic cross-sectional view showing another example of a substrate for cell transfer of the present invention.

Moreover, for example as shown in FIG. 4, the above-mentioned polymer base material 1 may have a concave portion or a convex portion which is formed in a pattern of the cell transfer layer 3. In this case, the cells can be cultured and transferred in a highly precise pattern by forming the cell transfer layer on only the above-mentioned convex portion or concave portion. The width of the concave portion or convex portion is generally about 10 μm to 500 μm, and it is more preferably about 20 μm to 200 μm. Moreover, the height of the above-mentioned concave portion or convex portion may be about 0.1 μm to 100 μm, and it is more preferably about 0.2 μm to 20 μm.

Here, the thickness of the above-mentioned polymer base material is preferably 1 μm to 250 μm, and more preferably 5 μm to 200 μm. When it is thinner than the above-mentioned range, due to the extremely high flexibility, handling can be extremely difficult, or due to the strength insufficiency, it can be torn or broken easily. Moreover, when the thickness is thicker than the above-mentioned range, due to the flexibility insufficiency, the adhesive properties with the transfer receptor can be poor at the time of transferring the cells cultured on the substrate for cell transfer.

4. Substrate for Cell Transfer

The substrate for cell transfer of the present invention is not particularly limited as long as it comprises the above-mentioned polymer base material, intermediate layer and cell transfer layer. As needed, it may optionally comprise other layer. For example, a cell transfer auxiliary layer, etc. may be formed on the above-mentioned cell transfer layer. Hereinafter, the cell transfer auxiliary layer used in the present invention will be explained.

(Cell•Transfer Auxiliary Layer)

The above-mentioned cell transfer auxiliary layer is formed on the cell transfer layer, and the cells are adhered onto the cell transfer auxiliary layer. After culturing the cells on the cell transfer auxiliary layer, at least a part of the cell transfer auxiliary layer is transferred onto the transfer receptor side, together with the cells, upon transferring the cells. In the present invention, since the cell transfer auxiliary layer is formed, the cells can be transferred onto the transfer receptor further efficiently. As the cell transfer auxiliary layer, those do not influence the transfer receptor side are selected. For example, a polypeptide such as a collagen, polysaccharides such as a hyaluronic acid, a polylactic acid, a polyglycolic acid, an arginic acid, a polyvinyl alcohol, a poly-lysine or the like can be presented. Moreover, in the above-mentioned cell transfer auxiliary layer, a metal ion such as a calcium ion and a magnesium ion may be contained.

B. Cell Transfer Substrate

Next, the cell transfer substrate of the present invention will be explained. The cell transfer substrate of the present invention comprises the cells adhered on the cell transfer layer of the above-mentioned substrate for cell transfer. For example, as shown in FIG. 2A, the cell transfer substrate of the present invention comprises a polymer base material 1; an intermediate layer 2 formed on the polymer base material 1; a cell transfer layer 3 formed on the intermediate layer 2; and cells 4 adhered on the cell transfer layer 3.

Since the above-mentioned intermediate layer is formed on the substrate for cell transfer mentioned above, the above-mentioned cell transfer layer is formed evenly. Therefore, according to the present invention, the cells can be cultured stably and adhered evenly on the cell transfer layer. Thus, with the cell transfer substrate, the cells cultured on the cell transfer layer can be transferred directly to the transfer receptor, maintaining the active state. Moreover, in the present invention, the cells can be transplanted onto the living body tissue or the like, maintaining the pattern as it is, even when: the size of the cultured cell pattern is extremely small; the cells are cultured sparsely; the cells are in a form of a small colony; or the cells are cultured in a pattern, for example, as a blood vessel, a vessel network such as a lymphatic vessel, or a nerve network.

Hereinafter, the cells used in the present invention will be explained.

1. Cells

The cells to be adhered on the above-mentioned cell transfer layer in the present invention may either be a floating cell such as a hemocyte cell and a lymphatic cell, or an adherent cell. In the present invention, cells having the adhesive properties are particularly preferable. As such cells having the adhesive properties, for example, a hepatocyte that is parenchymatous cell of the liver; an vascular endothelial cell; a fibroblast; an epidermal cell such as epidermal keratinocyte; an epithelial cell such as a trachea epithelial cell, a digestive tract epithelial cell, a cervical epithelial cell, and a lens epithelial cell; a mammary gland cell; a muscle cell such as a smooth muscle cell, and a cardiac muscle; a nephrocyte; a pancreatic Langerhans' cell; a nerve cell such as a peripheral nerve cell and an optic cell; a chondrocyte; an osteocyte or the like can be presented. These cells may either be a primary cell directly collected from a tissue or an organ, or those of after several generations. Moreover, they may be the established cell line. Furthermore, these cells may be any of an ES cell as an undifferentiated cell, a pluripotent stem cell having multipotency, a unipotent stem cell having the unipotency or a cell which have completed the differentiation. Moreover, the cells of a single kind may be cultured, or the cells of two or more kinds may be co-cultured.

2. Cell Transfer Substrate

The cell transfer substrate of the present invention is not particularly limited as long as it comprises the above-mentioned polymer base material, intermediate layer, cell transfer layer and cells. The cell transfer substrate of the present invention is used at the time of transferring the cells cultured on the above-mentioned cell transfer layer onto another culture substrate for processing or of transplanting the above-mentioned cells onto a living body tissue.

The present invention is not limited to the above-mentioned embodiments. The above-mentioned embodiments are merely examples, and any one having the substantially same configuration and achieves the same effects as the technological idea mentioned in the claims of the present invention is included in the technological scope of the present invention.

EXAMPLES

Hereinafter, with reference to the examples, the present invention will be explained further specifically.

Example 1

Formation of the Intermediate Layer

A 25 μm thickness polyester film was prepared. With the vacuum degree in a CVD chamber reduced to $4.0 \times 10^{-3}$ Pa, an electric power (input electric power 300 W) having a 90 kHz frequency was applied to the electrode. Thereafter, a hexamethyl disiloxane, an oxygen gas and a helium gas were introduced by each predetermined amount, and the vacuum degree was controlled to be 30 Mpa. Thereby, a silicon oxide based thin film (intermediate layer) was formed by about 100 nm thickness by plasma-enhanced vapor deposition (CVD method).

Formation of the Cell Transfer Layer 0.4 g of an organosilane TSL8114 (GE Toshiba Silicones) and 0.4 g of a fluoloalkyl silane TSL8233 (GE Toshiba silicones) were diluted by 5 g of an isopropyl alcohol and agitated for more than 15 minutes. A 1,3-butane diol was added to the above-mentioned solution and agitated for more than 15 minutes. The solution prepared accordingly was spin coated onto the above-mentioned intermediate layer and dried so as to provide a cell transfer layer. The average value of the contact angle of the cell transfer layer surface with water was 103.1°.

Production of the Photomask for the Exposure Treatment

A tetramethoxy silane and an HCl were mixed for more than 12 hours, and it was diluted by an isopropyl alcohol. The solution prepared accordingly was spin coated on the chromium pattern of a photomask having a line pattern with a 60 μm width opening part and a 300 μm width light-shielding portion disposed alternately, and then dried at 150° C.

Next, a solution prepared by adding a copper nitrate to a titanium oxide sol solution was spin coated on the above-mentioned mask and dried at 150° C. so as to form a photomask for the exposure treatment having a transparent photocatalyst-containing layer.

Exposure Treatment of the Cell Transfer Layer

With the photocatalyst-containing layer surface of the above-mentioned photomask for the exposure treatment and the above-mentioned cell transfer layer facing to each other, the ultraviolet ray irradiation was carried out from the photomask side, with a 14 J/cm$^2$ irradiation amount, using a mercury lamp. Thereby, a substrate for cell transfer, with a 60 μm width linear cell adhesion region and a 300 μm width cell adhesion-inhibiting region formed alternately, was obtained. The average value of the contact angle of the above-mentioned cell adhesion region surface with water was 21.7°.

(Cell Culture)

The above-mentioned substrate for cell transfer was sterilized using an autoclave by an ordinary method. As the cells, carotid endothelial cells derived from a bovine were used. With the substrate for cell transfer placed on a well plate, a MEM culture medium containing a 5% serum was added, and the cells were disseminated so as to be 1×10$^6$ cells/well. By culturing the same at 37° C. for 16 hours, a cell transfer substrate, with the cells adhered on the 60 μm width cell adhesion region with a high alignment properties, was obtained.

(Cell Transfer and Further Culture)

For the cell transfer, a prepared solubilized basement membrane extracted from EHS mouse tumor cell (hereinafter, it is also referred to as a cell transfer receiving functional material) was used. With the cell surface of the above-mentioned cell transfer substrate contacted with the cell transfer receiving functional material, a MEM culture medium containing 0.3% of a serum was added. After culturing the same at 37° C. for 5.5 hours, the cell transfer substrate was peeled off. Furthermore, it was cultured in the cell transfer receiving functional material for 12 hours. From an observation with a microscope, the cells were confirmed to be a luminal shape. Moreover, by measuring the number of the cells on the substrate in a predetermined region before and after the transfer, it was confirmed that 95% of the cells were transferred.

Example 2

Formation of the Intermediate Layer

In the same manner as in the example 1, a 65 nm film thickness silicon oxide based thin film containing a methyl group (intermediate layer) was formed on a 150 μm thickness polyester film.

Formation of the Cell Transfer Layer

After cleaning the above-mentioned intermediate layer surface with ultraviolet ray, a coating agent, prepared by diluting a silane coupling agent XC98-B2474 (GE Toshiba Silicones) 10-fold with an isopropyl alcohol, was coated on the surface by spin coating. Subsequently, by drying at 150° C. for 10 minutes, a substrate for cell transfer, provided with the cell transfer layer, was obtained. The average value of the contact angle of the above-mentioned cell transfer layer with water was 101.8°.

Production of the Photomask for the Exposure Treatment

A photomask with the blood vessel pattern based on a human eyeground blood vessel photograph as the opening part was produced. A photocatalyst-containing layer was formed on the photomask in the same manner as in the example 1.

Exposure Treatment of the Cell Transfer Layer

With the photocatalyst-containing layer surface of the above-mentioned photomask for the exposure treatment and the cell transfer layer facing with each other, the ultraviolet ray irradiation was carried out from the photomask for the exposure treatment side, with a 13 J/cm$^2$ irradiation amount, using a mercury lamp. Thereby, a substrate for cell transfer, comprising a cell adhesion region of the eyeground blood vessel pattern and a cell adhesion-inhibiting region other than the above, was obtained. The average value of the contact angle of the above-mentioned cell adhesion region with water was 25.2°.

(Cell Culture)

The above-mentioned substrate for cell transfer was sterilized using an autoclave by an ordinary method. As the cell, a human umbilical vein endothelial cell was used. With the above-mentioned substrate for cell transfer placed on a well plate, a RPMI culture medium containing 20% bovine fetus serum, a growth factor ECGS and a heparin was added, and the cells were disseminated so as to be 1×10$^6$ cells/well. By culturing the same at 37° C. for 16 hours, a cell transfer substrate, with the cells adhered on the 60 μm width cell adhesion region with a high alignment properties, was provided.

(Cell Transfer and Further Culture)

In the same manner as in the example 1, the cells were transferred onto the cell transfer receiving functional material, and the cells were confirmed to be a luminal shape. Moreover, by counting the number of the cells present in a predetermined region of the substrate for cell transfer and the number of the cells in a predetermined region of the cell transfer receiving functional material, the cell transfer ratio was 100%.

Example 3

Formation of the Intermediate Layer

An untreated polystyrene (PS) sheet having about a 20 mm diameter was prepared, and an intermediate layer was formed by the same method as in the example 1. By the oxygen plasma treatment, a silanol group was provided on the film surface.

Formation of the Cell Transfer Layer

The above-mentioned treated PS sheet was soaked quickly in a toluene solution (3% concentration) of a γ-methacryloxy propyl trimethoxy silane (GE Toshiba Silicones) for 2 hours. Thereafter, it was cleaned with a toluene and dried with a nitrogen gas. Subsequently, with the PS sheet placed in a 35 mm dish, a solution, prepared by diluting an N-isopropyl acrylic amide with an isopropyl alcohol to 55%, was spread on the above-mentioned PS sheet. By the electron beam irradiation to the PS sheet and further cleaning with water, a cell transfer layer comprising a poly(N-isopropyl acrylic amide) layer was formed on the intermediate layer.

Exposure Treatment of the Cell Transfer Layer

Using an ordinary photomask having a pattern of the negative-positive inversion of the example 1, a vacuum ultraviolet ray was irradiated to the above-mentioned cell transfer layer for 30 minutes to remove the poly(N-isopropyl acrylic amide) of the irradiated part, by oxidation decomposition, so as to provide a substrate for cell transfer.
(Cell Culture)

The substrate for cell transfer was sterilized with an ethylene oxide gas by an ordinary method. Thereafter, the cells were cultured on the substrate for cell transfer in the same conditions as the example 1 so as to provide a cell transfer substrate provided with a bovine blood vessel endothelial pattern.
(Cell Transfer and Further Culture)

Mouse osteoblast-like cells (MC3T3E1) were disseminated in a 10 cm dish, and after confirming the confluent state, the above was incubated for further 2 or more days so as to promote the extracellular matrix production. The cell transfer substrate provided with the above-mentioned bovine blood vessel endothelial pattern formed was placed gently onto the above-mentioned osteoblast cell sheet so as to have the cells facing with each other. Thereafter, the culture medium was poured gently into the dish. This state was maintained at 25° C. for 40 minutes. Thereafter, the dish was returned into the $CO_2$ incubator of 37° C., in a state with the blood vessel endothelial pattern sandwiched by the osteoblast cell sheet and the substrate for cell transfer, for carrying out the co-culture for 24 hours. Then, after removing only the substrate, culture was carried out for further 24 hours. From an observation with a microscope, it was confirmed that the endothelial cells were disposed in a pattern on the osteoblast-like cell layer and they have luminal shapes. Moreover, by counting the number of the cells present in a predetermined region of the substrate for cell transfer before and after the cell transfer, it was confirmed that 85% of the cells were transferred.

Example 4

Formation of the Intermediate Layer

With a porous polyester sheet having pores of an average 1 μm size placed in an oxygen plasma device, the pressure was reduced to $5 \times 10^{-5}$ Pa. With the oxygen pressure adjusted to 5 Pa, the oxygen plasma treatment was carried out for 10 minutes. On the treated porous polyester sheet, a 10 nm thickness silicon oxide based thin film containing a methyl group (intermediate layer) was formed in the same manner as in the example 1.

Formation of the Cell Transfer Layer

The above-mentioned intermediate layer was subjected to the oxygen plasma treatment. Thereafter, it was quickly placed in a Teflon (registered trademark) container (65 cm³ capacity) containing 0.2 cc of a heptadecafluoro-1,1,2,2-tetrahydrodecyl-1-trimethoxy silane (Shin-Etsu Chemical Co., Ltd.). The container was sealed and maintained in a 100° C. oven for 5 hours so as to form a cell transfer layer.

Exposure Treatment of the Cell Transfer Layer

Using the same photomask for the exposure treatment as the example 1, the ultraviolet ray irradiation was carried out from the photomask for the exposure treatment side, with a 14 J/cm² irradiation amount, using a mercury lamp. Thereby, a substrate for cell transfer, with a 60 μm width linear cell adhesion region and a 300 μm width cell adhesion-inhibiting region formed alternately, was obtained.
(Cell Culture, and Cell Transfer and Further Culture)

In the same manner as in the example 1, the cells were adhered onto the above-mentioned substrate for cell transfer and cultured. Then, the above was transferred onto the cell transfer receiving functional material. Thereby, the cells were confirmed to have luminal shapes. Moreover, by counting the number of the cells in a predetermined region of the substrate, the cell transfer ratio was confirmed to be 90%.

Example 5

Formation of the Intermediate Layer

Using a 15 μm thickness polylactic acid film, an intermediate layer was formed by the same method as in the example 1.

Formation of the Cell Transfer Layer

The above-mentioned intermediate layer surface was cleaned with a UV. Then, a silane coupling agent XC98-B2472 (GE Toshiba Silicones) was diluted 10-fold with an isopropyl alcohol, and a 1,3-butane diol was added thereto so as to have a 10% concentration, and then agitated. The coating solution was coated by the spin coat method, and dried at 55° C. for 24 hours. Thereafter, it was cleaned well with water and dried so as to provide a cell transfer layer. The average value of the contact angle of the cell transfer layer with water was 104.7°.

Exposure Treatment of the Cell Transfer Layer

Using the same photomask for the exposure treatment as the example 1, the ultraviolet ray irradiation was carried out from the photomask for the exposure treatment side, with a 14 J/cm² irradiation amount, using a mercury lamp. Thereby, a substrate for cell transfer, with a 60 μm width linear cell adhesion region and a 300 μm width cell adhesion-inhibiting region formed alternately, was obtained.
(Cell Culture)

After sterilizing the above-mentioned substrate for cell transfer with a 70% ethanol, the cells were cultured in the same manner as in the example 1. By adhering a blood vessel endothelial cell preliminarily fluorescent-dyed with PKH26 (Ardrich) onto the cell adhesion region, a cell transfer substrate was provided.
(Cell Transfer and Further Culture)

Under sterilized atmosphere, skin of the back part, the peritoneum and the liver extirpated from a nude mouse (5 days old, male) were placed in a 35 mm culture dish, and the subcutaneous tissue of the skin and the serous membrane of the liver were peeled off. Onto the extirpated tissues, the above-mentioned cell transfer substrate, on which the blood vessel endothelial cells adhere, was placed. 3 ml of a culture medium (5% bovine fetus serum containing MEM culture medium) was introduced into the culture dish, and the cells were cultured for 48 hours. Thereafter, the cell transfer substrate was removed with a pair of tweezers, and the endothelial cells were retained on the extirpated tissue. By observing a piece of the tissue with a microscope, it was confirmed that the blood vessel endothelial pattern was formed on the extirpated tissue. Moreover, by counting the number of the cells present in a predetermined region of the cell transfer substrate before the transfer and the number of the cells remaining in the predetermined region after the transfer, it was confirmed that 95% of the cells were transferred.

Example 6

Formation of the Minute Convexoconcave Intermediate Layer

A 23 mm diameter polyester sheet was cleaned with UV. Then, a cationic polymer adsorption layer was formed on the polyester sheet by soaking the sheet in a 0.2% solution of a polydiallyl dimethyl ammonium chloride (Aldrich) (containing 0.2 M sodium chloride) and cleaning with water. Then, an intermediate layer comprising a silica particle adsorption layer was formed by soaking the above-mentioned PET sheet in SPHERICA SLURRY S120 (CATALYSTS & CHEMICALS INC. CO., LTD.) and cleaning with water.

Formation of the Cell Transfer Layer

A coating solution, prepared by diluting silane coupling agent XC98-B2472 (GE Toshiba Silicones) 10-fold with an isopropyl alcohol, was coated onto the above-mentioned intermediate layer by the spin coating method, and dried at 150° C. for 15 hours so as to provide a cell transfer layer. The average value of the contact angle of the cell transfer layer with water was 137.2°.

Exposure Treatment of the Cell Transfer Layer

Using the same photomask for the exposure treatment as the example 1, the ultraviolet ray irradiation was carried out from the photomask for the exposure treatment side, with a 12 J/cm$^2$ irradiation amount, using a mercury lamp. Thereby, a substrate for cell transfer, with a 60 μm width linear cell adhesion region and a 300 μm width cell adhesion-inhibiting region formed alternately was obtained. The average value of the contact angle of the cell adhesion region with water was 20.0°.
(Cell Culture, and Cell Transfer and Further Culture)
In the same manner as in the example 1, the cells were adhered onto the above-mentioned substrate for cell transfer so as to provide a cell transfer substrate. The cells on the cell transfer substrate were transferred onto the cell transfer receiving functional material. Thereby, the cells were confirmed to have luminal shapes in the cell transfer receiving functional material. Moreover, by counting the number of the cells in a predetermined region before and after the cell transfer, the cell transfer ratio was confirmed to be 92%.

Example 7

Formation of the Intermediate Layer and Formation of the Cell Transfer Layer

After forming an intermediate layer in the same manner as in the example 1, a cell transfer layer was formed in the same manner as in the example 6. The average value of the contact angle of the cell transfer layer with water was 102.2°.

Production of the Photomask for the Exposure Treatment

By the same procedure as in the example 1, a photomask for the exposure treatment comprising a transparent photocatalyst-containing layer, having a dot pattern wherein a large number of 18 mm diameter circular opening parts arranged by a 20 mm interval in the light-shielding portion, was formed.

Exposure Treatment of the Cell Transfer Layer

With the photocatalyst-containing layer surface of the above-mentioned photomask for the exposure treatment and the above-mentioned cell transfer layer facing with each other, the ultraviolet ray irradiation was carried out from the photomask for the exposure treatment side, with a 4 J/cm$^2$ irradiation amount, using a mercury lamp so as to obtain a substrate for cell transfer with a 18 mm diameter circular cell adhesion regions and a cell adhesion region formed in the periphery thereof. The average value of the contact angle of the cell adhesion region with water was 49.6°.

Then, the substrate for cell transfer was cut out by a 7.5 cm square. In this case, the cut out substrate for cell transfer included four regions of the cell adhesion region.
(Cell Culture)
The substrate for cell transfer was sterilized, with an autoclave, by an ordinary method. As the cells, carotid endothelial cells derived from a bovine were used. With the above-mentioned substrate for cell transfer placed on a square dish, a MEM culture medium containing a 5% serum was added, and the cells were disseminated so as to be 1×10$^6$ cells/well. By culturing the same at 37° C. for 16 hours, a cell transfer substrate, with the endothelial cells adhered confluent only in the circular cell adhesion region, was provided.
(Cell Transfer and Further Culture)
For the cell transfer, a prepared solubilized basement membrane extracted from EHS mouse tumor cell (hereinafter, it is also referred to as a cell transfer receiving functional material) was used. With the cell surface of the above-mentioned cell transfer substrate contacted with the cell transfer receiving functional material, a MEM culture medium containing 0.3% of a serum was added. After culturing the same at 37° C. for 5.5 hours, the cell transfer substrate was peeled off. Furthermore, it was cultured in the cell transfer receiving functional material for 24 hours. During the culture, the blood vessel endothelial cells were partially re-aligned so as to have luminal shapes. Moreover, by measuring the number of the cells in a predetermined region before and after the cell transfer, it was confirmed that 80% of the cells were transferred.

Example 8

Formation of the Cell Transfer Layer (Reaction in the First Stage)
The intermediate layer surface, of the base material provided with the intermediate layer wherein a silicon oxide based thin film (intermediate layer) is formed by a 100 nm thickness on a 25 μm polyester, produced in the example 1, was cleaned with UV. 39.0 g of toluene and 13.5 g of silane coupling agent TSL8350 (GE Toshiba Silicones) were mixed, and while agitating the same, 450 μl of triethyl amine was added thereto. After agitating as it is for several minutes at room temperature, the total amount was moved to a glass dish. The above-mentioned base material provided with the intermediate layer after UV cleaning was soaked herein and left at room temperature for 16 hours. Thereafter, the base material provided with the intermediate layer was cleaned with ethanol and water, and dried. Thereby, a thin film containing an epoxy group was formed on the intermediate layer surface.

(Reaction in the Second Stage)

While agitating 50 g of tetraethylene glycol, 250 µl of a concentrated sulfuric acid was added dropwise. After agitating as it is for several minutes, the total amount was moved to a glass dish. The above-mentioned base material provided with the intermediate layer was soaked herein and reacted at 80° C. for 30 minutes. After the reaction, the above-mentioned base material provided with the intermediate layer was cleaned well with water and dried. Thereby, an even hydrophilic thin film as the cell transfer layer was formed on the intermediate layer surface.

Exposure Treatment of the Cell Transfer Layer

In the same manner as in the example 1, the ultraviolet ray irradiation was carried out with a 10 J/cm$^2$ irradiation amount. Thereby, a substrate for cell transfer, with a 60 µm width linear cell adhesion region and a 300 µm width cell adhesion-inhibiting region formed alternately was obtained. The average value of the contact angle of the above-mentioned cell adhesion region surface with water was 15.8°.

(Cell Culture)

The above-mentioned substrate for cell transfer was sterilized, with an autoclave, by an ordinary method. As the cells, human umbilical vein endothelial cells (HUVEC, KURABO INDUSTRIES LTD.) were used. With the above-mentioned substrate for cell transfer placed on a well plate, HuMedia-EG2 (KURABO INDUSTRIES LTD.) as a low serum culture medium for a normal human blood vessel endothelial cell was added, and the cells were disseminated so as to be 1×10$^6$ cells/well. By culturing the same in 5% $CO_2$ concentration incubator at 37° C. for 46 hours, so as to adhere the HUVEC only to the cell adhesion region in a confluent state, a cell transfer substrate was obtained.

(Cell Transfer and Further Culture)

The above-mentioned cell transfer substrate and a growth factor reducing matrigel (Becton Dickinson) were contacted such that the cell surface faces to the matrigel and maintained for several minutes. Thereafter, the HuMedia-EG2 was placed in a culture container and cultured for 2 hours in 5% $CO_2$ concentration incubator, at 37° C. From an observation with a phase-contrast microscope, it was confirmed that the HUVEC have been morphology changed so as to have tubular shape. Thereafter, only the substrate for cell transfer was peeled off, and the substrate for cell transfer was peeled off easily so that the HUVEC was retained on the matrigel. From the observation with a phase-contrast microscope, it was confirmed that the tubular shape of the HUVEC was barely disturbed. Moreover, by counting the number of the cells on the substrate in a predetermined region before and after the transfer, it was confirmed that substantially 100% of the cells were transferred onto the matrigel.

Example 9

Formation of the Cell Transfer Layer (Reaction in the First Stage)

The intermediate layer surface of the base material provided with the intermediate layer, wherein a silicon oxide based thin film (intermediate layer) formed by a 65 nm thickness on a 150 µm thickness polyester, produced in the example 2 was cleaned with UV. 39.0 g of a toluene and 13.5 g of a silane coupling agent TSL8350 (GE Toshiba Silicones) were mixed, and while agitating the same, 450 µl of triethyl amine was added thereto. After agitating as it is for several minutes at room temperature, the total amount was moved to a glass dish. The above-mentioned base material provided with the intermediate layer after UV cleaning was soaked herein and left at room temperature for 16 hours. Thereafter, the above-mentioned base material provided with the intermediate layer was cleaned with an ethanol and water, and dried. Thereby, a thin film containing an epoxy group was formed on the intermediate layer surface.

(Reaction in the Second Stage)

While agitating 50 g of a polyethylene glycol having average molecular weight of 400 (PEG400), 25 µl of concentrated sulfuric acid was added dropwise. After agitating as it is for several minutes, the total amount was moved to a glass dish. The above-mentioned base material provided with the intermediate layer was soaked herein and reacted at 80° C. for 20 minutes. After the reaction, the above-mentioned base material provided with the intermediate layer was cleaned well with water and dried. Thereby, an even hydrophilic thin film as the cell transfer layer was formed on the intermediate layer surface.

Exposure Treatment of the Cell Transfer Layer

In the same manner as in the example 1, the ultraviolet ray irradiation was carried out with 10 J/cm$^2$ irradiation amount. Thereby, a substrate for cell transfer, with a 60 µm width linear cell adhesion region and a 300 µm width cell adhesion-inhibiting region formed alternately was obtained. The average value of the contact angle of the above-mentioned cell adhesion region surface with water was 17.2°.

(Cell Culture)

The above-mentioned substrate for cell transfer was sterilized, with an autoclave, by an ordinary method. In the same manner as in the example 8, with the HuMedia-EG2 (KURABO INDUSTRIES LTD.) added to a well plate, a human umbilical vein endothelial cells (HUVEC, KURABO INDUSTRIES LTD.) were disseminated so as to be 1×10$^6$ cells/well. By culturing the same in 5% $CO_2$ concentration incubator, at 37° C., for 46 hours, a cell transfer substrate, with HUVEC adhered in confluent state only in the cell adhesion region, was provided.

(Cell Transfer and Further Culture)

The above-mentioned cell transfer substrate and a growth factor reducing matrigel (Becton Dickinson) were contacted such that the cell surface faces to the matrigel. Thereafter, the HuMedia-EG2 was placed in a culture container and cultured for 2 hours in 5% $CO_2$ concentration incubator at 37° C. From the observation with a phase-contrast microscope, it was confirmed that the HUVEC have been morphology changed so as to have tubular shape. Thereafter, only the substrate for cell transfer was peeled off, and the substrate for cell transfer was peeled off easily so that the HUVEC was retained on the matrigel. From the observation with a phase-contrast microscope, it was confirmed that the tubular shape of the HUVEC was barely disturbed. Moreover, by counting the number of the cells on the substrate in a predetermined region before and after the transfer, it was confirmed that substantially 100% of the cells were transferred onto the matrigel.

Example 10

Culture of the Fibroblast

A fibroblast of a mouse embryo BALB/3T3 clone A31 was cultured in a 6 cm dish with a DMEM culture medium containing a 10% bovine fetus serum. After confirmation of the 100% confluent state, it was cultured for further 24 hours.
(Fluorescent Dyeing of the Bovine Blood Vessel Endothelial Cells)

The bovine blood vessel endothelial cells (bEC) were fluorescent-dyed using fluorescent dye PKH26 (produced by Ardrich). As to the dyeing method, it was carried out according to the protocol sheet of the manufacturer.
(Pattern Culture of the Fluorescent-Dyed bEC)

MEM culture medium containing a 5% bovine fetus serum was added to the substrate for cell transfer produced in the example 8, the fluorescent-dyed bEC was disseminated, and the same was cultured in a pattern for 48 hours in an incubator (37° C., 5% $CO_2$) so as to provide a cell transfer substrate. From the phase-contrast microscope observation, it was confirmed that the cell pattern was preferable. Moreover, from the fluorescence microscope observation, it was confirmed that the bEC was dyed preferably.
(Cell Transfer and Further Culture)

The culture medium was vacuumed and removed from the dish on which the above-mentioned fibroblast being cultured. Then, the above-mentioned cell transfer substrate, on which the above-mentioned fluorescent-dyed bEC was cultured in a pattern, was disposed such that the fibroblast sheet and the pattern-cultured bEC face with each other. Then, with the lid of the dish closed, it was retained in the incubator for 10 minutes. Thereafter, a 0.3% bovine serum containing MEM culture medium was added carefully into the dish without moving the substrate. Furthermore, it was cultured in the incubator for 6 hours. From the fluorescence microscope observation, it was confirmed that the width of the bEC pattern was narrowed by about 50%. Moreover, by carefully peeling off the substrate for cell transfer, it was confirmed by the microscope observation that the bEC pattern was transferred onto the fibroblast sheet, and the bEC was not remained on the substrate for cell culture.

What is claimed is:

1. A substrate for cell transfer comprising:
    a polymer base material;
    an intermediate layer formed on the polymer base material, wherein the intermediate layer comprises a composite substance selected from the group consisting of polyethylene imine and polyallyl amine; and
    a cell transfer layer formed on the intermediate layer, wherein the cell transfer layer is a layer containing a polyethylene glycol-polypropylene glycol block copolymer.
2. The substrate for cell transfer according to claim 1, wherein the cell transfer layer is a layer containing a thermosensitive polymer.
3. The substrate for cell transfer according to claim 1, wherein a surface roughness of the intermediate layer is in a range of 5 nm to 300 nm.
4. A cell transfer substrate, wherein a cell is adhered to the cell transfer layer of the substrate for cell transfer according to claim 1.
5. A cell transfer substrate, wherein a cell is adhered to the cell transfer layer of the substrate for cell transfer according to claim 2.
6. A cell transfer substrate, wherein a cell is adhered to the cell transfer layer of the substrate for cell transfer according to claim 3.
7. The substrate for cell transfer according to claim 1, wherein the intermediate layer comprises polyallyl amine.
8. The substrate for cell transfer according to claim 1, wherein the intermediate layer comprises polyethylene imine.
9. The substrate for cell transfer according to claim 1, wherein the polymer base material is selected from the group consisting of polypropylene, polymethyl pentene, polypropylene copolymer, ethylene-tetrafluoroethylene copolymer, polycarbonate, acetal resin, polysulfone, polyvinyl chloride, silicone resin, polystyrene, styrene-acrylonitrile copolymer, methyl polymethacrylate, polyurethane, polyester, polyimide, polyglycol acid, polylactic acid, and collagen.
10. The substrate for cell transfer according to claim 9, wherein the polymer base material is selected from the group consisting of polymethyl pentene, polycarbonate, polyvinyl chloride, polyester, polyimide, and polyglycol acid.
11. The substrate for cell transfer according to claim 10, wherein the polymer base material is selected from the group consisting of polycarbonate and polyimide.
12. The substrate for cell transfer according to claim 11, wherein the polymer base material comprises polymethyl pentene.
13. A substrate for cell transfer comprising:
    a polymer base material comprising polycarbonate;
    an intermediate layer formed on the polymer base material, wherein the intermediate layer comprises polyallyl amine; and
    a cell transfer layer formed on the intermediate layer, wherein the cell transfer layer comprises a polyethylene glycol-polypropylene glycol block copolymer.
14. A substrate for cell transfer comprising:
    a polymer base material comprising polyimide;
    an intermediate layer formed on the polymer base material, wherein the intermediate layer comprises polyethylene imine; and
    a cell transfer layer formed on the intermediate layer, wherein the cell transfer layer comprises a polyethylene glycol-polypropylene glycol block copolymer.

* * * * *